United States Patent [19]
Ansai et al.

[11] Patent Number: 5,420,098
[45] Date of Patent: May 30, 1995

[54] HERBICIDAL COMPOSITION COMPRISING HW-52 AND ONE OF ATRAZINE, CYANAZINE, IOXYNIL, BROMOXYNIL, OR METRIBUZIN

[75] Inventors: Tatsuo Ansai; Yukihiko Inayoshi; Shihoko Aizawa, all of Tsukuba, Japan

[73] Assignee: Hodogaya Chemical Co., Ltd., Tokyo, Japan

[21] Appl. No.: 220,703

[22] Filed: Mar. 31, 1994

[30] Foreign Application Priority Data

Mar. 31, 1993 [JP] Japan .................................. 5-095006

[51] Int. Cl.$^6$ ...................... A01N 37/22; A01N 37/34; A01N 43/70; A01N 43/707
[52] U.S. Cl. ..................................... 504/133; 504/141; 504/142; 504/149
[58] Field of Search ................. 504/133, 141, 142, 149

[56] References Cited

U.S. PATENT DOCUMENTS 4,937,386 6/1990 Ueda et al. ............................ 568/31

OTHER PUBLICATIONS

Hoya Corp '303 (JP 82-85,303; May 28, 1982) in CA97:1220756b.
Hoya Corp '307 (JP 82-80,307; May 19, 1982) in CA97:1220686b.
Central Patent Index, Basic Abstracts Journal, Derwent Publications, Ltd., AN-53155, JP-A-57 080 307, May 19, 1982.

*Primary Examiner*—S. Mark Clardy
*Attorney, Agent, or Firm*—Oblon, Spivak, McClelland, Maier & Neustadt

[57] ABSTRACT

A herbicidal composition comprising, as active ingredients, 2',3'-dichloro-4-ethoxymethoxybenzanilide (compound 1) and one member selected from the group consisting of 2-chloro-4-ethylamino-6-isopropylamino-1,3,5-triazine (compound 2, atrazine), 2-(4-chloro-6-ethylamino-1,3,5-triazin-2-yl)amino-2-methylpropionitrile compound 3, cyanazine), 4-hydroxy-3,5-diiodobenzonitrile (compound 4, ioxynil), 4-octanoyloxy-3,5-dibromobenzonitrile (compound 5, bromoxynil), 2-(2-chloro-4-mesylbenzoyl)cyclohexane-1,3-dione (compound 6) and 4-amino-6-tert-butyl-3-methylthio-1,2,4-triazine-5(4H)-one (compound 7, metribuzin).

7 Claims, No Drawings

HERBICIDAL COMPOSITION COMPRISING HW-52 AND ONE OF ATRAZINE, CYANAZINE, IOXYNIL, BROMOXYNIL, OR METRIBUZIN

The present invention relates to a herbicidal composition.

There are very many kinds of weeds to be controlled in cultivation fields of gramineous crop plants or in lawn fields. They include annual gramineous weeds and annual broadleaf weeds as roughly classified. Among them, gramineous weeds are difficult to selectively control, as gramineous weeds and gramineous crop plants are alike, and yet gramineous weeds germinate abundantly. Therefore, if gramineous weeds remain, there will be a problem that the yield will be poor in such cultivation fields. At present, it is common to control gramineous weeds by applying a soil-treating agent prior to germination of weeds. However, such a method has a drawback such that the period for the application is rather short. On the other hand, foliage treating agents are not many which are useful for controlling gramineous weeds, and presently available foliage treating agents have such a problem that they are likely to bring about phytotoxicity to crop plants. Therefore, it has been desired to develop an excellent foliage treating agent.

2',3'-Dichloro-4-ethoxymethoxybenzanilide (hereinafter referred to as compound 1) is a known compound, and it is known as a herbicide for rice fields (Japanese Unexamined Patent Publication No. 73055/1981, CA: 79540-50-4 (1979)).

On the other hand, 2-chloro-4-ethylamino-6-isopropylamino-1,3,5-triazine (hereinafter referred to as compound 2) is widely used as a herbicide for corn and sorghum and as a herbicide for lawn. Further, 2-(4-chloro-6-ethylamino-1,3,5-triazin-2-yl)amino-2-methylpropiononitrile (hereinafter referred to as compound 3) is widely used as a herbicide for corn, barley, wheat, oats, rye or the like and as a herbicide for lawn. At usual doses, compounds 2 and 3 exhibit strong herbicidal effects against annual gramineous weeds and annual broadleaf weeds as soil treating agents. However, in the foliage treatment, they have a drawback that their herbicidal effects are weak against annual gramineous weeds, although they show strong herbicidal effects against annual broadleaf weeds.

4-Hydroxy-3,5-diiodobenzonitrile (hereinafter referred to as compound 4) is widely used as a herbicide for corn and sorghum, as a herbicide for lawn and as a herbicide for barley, wheat, oats, rye or the like. Further, 4-octanoyloxy-3,5-dibromo-benzonitrile (hereinafter referred to as compound 5) is widely used as a herbicide for barley, wheat, oats, rye or the like, as a herbicide for corn and sorghum and as a herbicide for lawn. At usual doses, compounds 4 and 5 exhibit strong herbicidal effects against annual broadleaf weeds as foliage treating agents, but they have a drawback that their herbicidal effects are very weak against annual gramineous weeds.

2-(2-Chloro-4-mesylbenzoyl)cyclohexane-1,3-dione (hereinafter referred to as compound 6) is a herbicide which is presently being developed as a herbicide for corn. At a usual dose, compound 6 exhibits strong herbicidal effects against annual broadleaf weeds and crabgrass (Digitaria adscendens) being an annual gramineous weed, as a foliage treating agent, but it has a drawback that its herbicidal effects are very weak against greenfoxtail (Setaria viridis) being an annual gramineous weed.

4-Amino-6-tert-butyl-3-methylthio-1,2,4-triazine-5(4H)-one (hereinafter referred to as compound 7) is a herbicide which is presently used as a foliage herbicide for corn. At a usual dose, compound 7 exhibits strong herbicidal effects against annual broadleaf weeds as a foliage treating agent, but it has a drawback that its herbicidal effects are very weak against annual gramineous weeds.

Herbicides presently used in corn fields as soil treating agents prior to germination of weeds and as foliage treating agents useful from germination to the initial growing stage, are mostly compounds 2 and 3. However, as a foliage treating agent for corn which is intended to control gramineous weeds, 2-(3,5-dichlorophenyl)-2-(2,2,2-trichloroethyl)oxylene (hereinafter referred to as compound A) may be mentioned. In the corn fields, it is common to employ a mixture of compound A and compound 2 or 3 for the purpose of controlling both annual broadleaf weeds and annual gramineous weeds. However, depending upon the weather conditions or growing conditions, it may happen that gramineous weeds substantially remain, or phytotoxicity to corn will be brought about.

On the other hand, many foliage treating agents are presently available which are intended to control annual broadleaf weeds and annual gramineous weeds in cultivation fields of barley, wheat, oats, rye or the like. As a widely used herbicide, 3-(4-isopropyl)-1,1-dimethylurea (hereinafter referred to as compound B) may be mentioned, but it is likely to bring about phytotoxicity against barley, wheat, oats, rye or the like, depending upon the weather conditions or growing conditions.

The present inventors have studied mixing of various herbicides to solve these problems, and as a result, have found that a combination of compound 1 and one member selected from the group consisting of compounds 2 to 7 exhibits synergistic effects far superior to the herbicidal effects obtainable by single use of each compound. Further, detailed studies have been made on the doses, the blend ratios, the application fields, the effects and the phytotoxicity against crop plants in order to make such synergistic effects practically useful. The present invention has thus been accomplished.

Thus, the present invention provides a herbicidal composition comprising, as active ingredients, 2',3'-dichloro-4-ethoxymethoxybenzanilide (compound 1) and one member selected from the group consisting of 2-chloro-4-ethylamino-6-isopropylamino-1,3,5-triazine (compound 2), 2-(4-chloro-6-ethylamino-1,3,5-triazin-2-yl)amino-2-methylpropiononitrile (compound 3), 4-hydroxy-3,5-diiodobenzonitrile (compound 4), 4-octanoyloxy-3,5-dibromobenzonitrile (compound 5), 2-(2-chloro-4-mesylbenzoyl)cyclohexane-1,3-dione (compound 6) and 4-amino-6-tert-butyl-3-methylthio-1,2,4-triazine-5(4H)-one (compound 7).

The synergistic effects according to the present invention were observed over a wide range from a low dose to a high dose.

In the case of a combination of compound 1 with compound 2 or 3, remarkable synergistic effects were observed widely against annual gramineous weeds such as crabgrass (Digitaria adscendens) and greenfoxtail (Setaria viridis) and annual broadleaf weeds such as pigweed (Amaranthus retroflexus) and velvetleaf (Abtilon theophrasti). Whereas, there was no synergistic increase of phytotoxicity against corn, or barley, wheat, oats, rye or the like, and the selectivity between crop plants and weeds was maintained. For example, in the case of a combination of compound 1 with compound 3, slight phytotoxicity was observed, but such phytotoxicity was practically negligible at a level equal to the phytotoxicity by single use of compound 3.

With respect to a combination of compound 1 with compound 4 or 5, remarkable synergistic effects were observed widely against annual gramineous weeds such as crabgrass (*Digitaria adscendens*), greenfoxtail (*Setaria viridis*) and water foxtail (*Alopecurus aequalis*), and annual broadleaf weeds such as pigweed (*Amaranthus retroflexus*), lambsquater (*Chenopodium album*) and chickweed (*Stellaria media*). Whereas, there was no synergistic increase of phytotoxicity against corn, or barley, wheat, oats, rye or the like, or lawn grasses, and thus the selectivity between crop plants and weeds was maintained. For example, in the case of a mixture of compound 1 with compound 4 or 5, slight phytotoxicity was observed, but such phytotoxicity was practically negligible at a level equal to the phytotoxicity by single use of compound 4 or 5.

With respect to a combination of compound 1 with compound 6, remarkable synergistic effects were observed widely against annual gramineous weeds such as crabgrass (*Digitaria adscendens*) and greenfoxtail (*Setaria viridis*), and annual broadleaf weeds such as pigweed (*Amaranthus retroflexus*), lambsquater (*Chenopodium album*) and black nightshade (*Solanum nigrum L.*). Whereas, no synergistic increase of phytotoxicity to corn was observed, and thus the selectivity between crop plants and weeds was maintained.

With respect to a combination of compound 1 with compound 7, remarkable synergistic effects were observed widely against annual gramineous weeds such as crabgrass (*Digitaria adscendens*) and greenfoxtail (*Setaria viridis*), and annual broadleaf weeds such as cocklebur (*Xanthium strumarium*), morningglory (*Ipomoea hederacea*) and pigweed (*Amaranthus retroflexus*). Whereas, no synergistic increase of phytotoxicity against corn was observed, and thus the selectivity between crop plants and weeds was maintained.

The doses of the respective components constituting the herbicidal compositions of the present invention may be such that compound 1 is from 10 to 200 g/10a, preferably from 25 to 100 g/10a; each of compounds 2 and 3 is from 10 to 200 g/10a, preferably from 25 to 100 g/10a; each of compounds 4 and 5 is from 5 to 100 g/10a, preferably from 6 to 50 g/10a; compound 6 is from 5 to 100 g/10a, preferably from 10 to 50 g/10a; and compound 7 is from 1 to 25 g/10a, preferably from 5 to 25 g/10a. However, the total dose is not required to exceed 200 g/10a and is usually about 100 g/10a.

In the herbicidal composition of the present invention, the ratio of active compound 1 to active compound 2, 3, 4, 5, 6 or 7 may be suitably selected within a range where the excellent selectivity for crop plants according to the present invention is not substantially impaired. For example, the weight ratio of compound 1:compound 2 is selected within a range of from 1:0.1 to 1:10, preferably from 1:0.25 to 1:4. Likewise, the weight ratio of compound 1:compound 3 may be selected within a range of from 1:0.1 to 1:10, preferably from 1:0.25 to 1:4. The weight ratio of compound 1:compound 4 may be selected within a range of from 1:0.01 to 1:1, preferably from 1:0.1 to 1:0.5. The weight ratio of compound 1:compound 5 may be selected within a range of from 1:0.01 to 1:1, preferably from 1:0.1 to 1:0.5. The weight ratio of compound 1:compound 6 may be selected with a range of from 1:0.025 to 1:10, preferably from 1:0.1 to 1:2. The weight ratio of compound 1:compound 7 may be selected within a range of from 1:0.01 to 1:1, preferably from 1:0.1 to 1:1.

The herbicidal composition of the present invention thereby provides herbicidal effects advantageously and certainly in the field under natural conditions, and thus it has been confirmed that the herbicidal composition of the present invention has a very high practical value.

For the application of the composition of the present invention, the active compounds may be blended at site or preliminarily combined to form a unitary formulation. In the case of the unitary formulation, the composition may be in the form of a formulation which can well be deposited on the foliage, such as a wettable powder, a water-dispersible granule or a sol.

The carrier to be used for the composition may be an inert inorganic substance such as water, bentonite, zeolite, calcium carbonate or sodium chloride.

As a dispersing agent or a solidifying agent, various surfactants such as an alkylnaphthalenesulfonic acid/formalin condensation product, a dialkylsulfosuccinate, a polyoxyethylene alkylaryl ether, a polyoxyethylene lauryl ether, a polyoxyethylene alkylaryl ether, and polyoxyethylene dodecyl ether, may be mentioned.

Further, adjuvants such as a thickener, a defoamer and a stabilizer may suitably be selected for incorporation.

Now, the present invention will be described in further detail with reference to Examples which include Formulation Examples and Test Examples. However, it should be understood that the present invention is by no means restricted by such specific Examples.

Now, the composition of the present invention will be specifically described with reference to Formulation Examples for separate formulations. In the following description, "parts" means "parts by weight", and "%" means "% by weight".

FORMULATION EXAMPLE 1

Preparation of a Wettable Powder (Single Formulation of Compound 1)

30 Parts of clay and 2 parts of white carbon were added to 50 parts of compound 1, followed by pulverization in a jet mill. Then, 12 parts of clay was added thereto and uniformly mixed. Then, 5 parts of powdery surfactant Sorpol 5039 (trademark of Toho Chemical Industry Co., Ltd.; polyoxyethylene alkylaryl ether sulfate) and 1 part of Rapisol BB75 (trademark of Nippon Oil and Fats Co., Ltd.) were added thereto and thoroughly mixed to obtain a wettable powder containing 50% of compound 1.

FORMULATION EXAMPLE 2

Preparation of a Water Dispersible Granule (Combination of Compounds 1 and 2)

30 Parts of compound 2, 10 parts of white carbon, 4 parts of Sorpol 5039 (trademark of Toho Chemical Industry Co., Ltd.), 1 part of Vannox PW (trademark of Nippon Nyukazai K.K.) and 24 parts of sodium tripolyphosphate were added to 30 parts of compound 1, and 10 parts of water were further added thereto. The mixture was extruded and granulated by a granulating machine, then dried and sieved to obtain a water dispersible granule of from 10 to 48 mesh.

FORMULATION EXAMPLE 3

Preparation of a Sol (Combination of Compounds 1 and 3)

48.3 Parts of water was added to 25 parts of compound 1 and 15 parts of compound 3. Then, 7 parts of Sorpol 3742 (trademark of Toho Chemical Industry Co., Ltd.) as a surfactant and 0.5 part of Sorpol 5712 (trademark of Toho Chemical Industry Co., Ltd.) as a defoaming agent were added thereto. The mixture was pulverized in a sand grinder and withdrawn. Then, 4 parts of ethylene glycol and 0.2 part of VANGEL-B (trademark of Sanyo Kasei K.K.) were added thereto as stabilizers and thoroughly stirred to obtain a sol containing 25% of compound 1 and 15% of compound 3.

FORMULATION EXAMPLE 4

Preparation of a Water Dispersible Granule (Combination of Compounds 1 and 4)

20 Parts of compound 4, 2 parts of white carbon, 8 parts of clay, 4 parts of Sorpol 5039 (trademark of Toho Chemical Industry Co., Ltd.), 1 part of Vannox PW (trademark of Nippon Nyukazai K.K.) and 25 parts of sodium tripolyphosphate were added to 40 parts of compound 1. Then, 10 parts of water was further added thereto. The mixture was extruded and granulated by a granulating machine, then dried and sieved to obtain a water dispersible granule of from 10 to 48 mesh.

FORMULATION EXAMPLE 5

Preparation of an Emulsifiable Concentrate (Combination of Compounds 1 and 5)

20 Parts of compound 1 and 10 parts of compound 5 were dissolved in 20 parts of xylene and 40 parts of cyclohexanone, and 10 parts of Sorpol 800A was added thereto and stirred and dissolved to obtain an emulsifiable concentrate containing 20 parts of compound 1 and 10 parts of compound 5.

FORMULATION EXAMPLE 6

Preparation of a Water Dispersible Granule (Combination of Compounds 1 and 6)

22.5 Parts of compound 6, 5 parts of white carbon, 17.5 parts of kaolin clay, 4 parts of Sorpol 5039 (trademark of Toho Chemical Industry Co., Ltd..), 1 part of Vannox PW (trademark of Nippon Nyukazai K.K.) and 25 parts of sodium tripolyphosphate were added to 25 parts of compound 1, and 10 parts of water was further added thereto. The mixture was extruded and granulated by a granulating machine, then dried and sieved to obtain a water dispersible granule of from 10 to 48 mesh.

FORMULATION EXAMPLE 7

Preparation of an Emulsifiable Concentrate (Combination of Compounds 1 and 6)

25 Parts of compound 1 and 15 parts of compound 6 were dissolved in 10 parts of xylene and 40 parts of cyclohexanone, and 10 parts of Sorpol 800A was added thereto and stirred and dissolved to obtain an emulsifiable concentrate containing 25 parts of compound 1 and 15 parts of compound 6.

FORMULATION EXAMPLE 8

Preparation of a Sol (Combination of Compounds 1 and 6)

35.8 Parts of water, 7 parts of Sorpol 3742 (trademark of Toho Chemical Industry Co., Ltd.) as a surfactant and 0.5 part of Sorpol 5712 (trademark of Toho Chemical Industry Co., Ltd.) as a defoaming agent, were added to 37.5 parts of compound 1 and 15 parts of compound 6, and the mixture was pulverized in a sand grinder and taken out. Then, 4 parts of ethylene glycol and 0.2 part of VANGEL-B (trademark of Sanyo Kasei K.K.) were added thereto as stabilizers and thoroughly mixed to obtain a sol containing 37.5 parts of compound 1 and 15 parts of compound 6.

FORMULATION EXAMPLE 9

Preparation of a Water Dispersible Granule (Combination of Compounds 1 and 7)

10 Parts of compound 7, 5 parts of white carbon, 30 parts of kaolin clay, 4 parts of Sorpol 5039 (trademark of Toho Chemical Industry Co., Ltd.), 1 part of Vannox PW (trademark of Nippon Nyukazai K.K.) and 25 parts of sodium tripolyphosphate were added to 25 parts of compound 1, and 10 parts of water was further added thereto. The mixture was extruded and granulated by a granulating machine, then dried and sieved to obtain a water dispersible granule of from 10 to 48 mesh.

FORMULATION EXAMPLE 10

Preparation of an Emulsifiable Concentrate (Combination of Compounds 1 and 7)

25 Parts of compound 1 and 10 parts of compound 7 were dissolved in 17.5 parts of xylene and 40 parts of cyclohexanone, and 10 parts of Sorpol 800A was added thereto and stirred and dissolved to obtain an emulsifiable concentrate containing 25 parts of compound 1 and 7.5 parts of compound 7.

FORMULATION EXAMPLE 11

Preparation of a Sol (Combination of Compounds 1 and 7)

40.8 Parts of water, 7 parts of Sorpol 3742 (trademark of Toho Chemical Industry Co., Ltd.) as a surfactant and 0.5 part of Sorpol 5712 (trademark of Toho Chemical Industry Co., Ltd.) as a defoaming agent, were added to 37.5 parts of compound 1 and 10 parts of compound 7, and the mixture was pulverized in a sand grinder and then taken out. Then, 4 parts of ethylene glycol and 0.2 part of VANGEL-B (trademark of Sanyo Kasei K.K.) were added thereto as stabilizers and thoroughly stirred to obtain a sol containing 37.5 parts of compound 1 and 15 parts of compound 7.

Now, the herbicidal effects of the herbicides of the present invention will be described in detail with reference to Test Examples.

TEST EXAMPLE 1

Test in a Pot in a Greenhouse

To a solution having a predetermined concentration of a single formulation of compound 1 or a mixture of a single formulation of compound 1 with a single formulation of compound 2 or 3 prepared in accordance with Formulation Example 1, a spreader was added so that its concentration would be 300 ppm at the time of application. Such a solution was applied by a spray gun at a rate of 100 l/10a over various plants grown to 3 to 4 leaf stage in a polypropylene pot having a surface area of 150 cm².

One month after the application, an investigation was carried out by visual observation. The results are shown in Tables 1 and 2.

The results of the investigation by visual observation are represented by the following evaluation standards.

Evaluation Standards of the Herbicidal Effects

0: No herbicidal effects
1: 20% control
2: 40% control
3: 60% control
4: 80% control
5: Completely controlled Evaluation Standards for Phytotoxicity to Crop Plats 0: No phytotoxicity
1: Slight degree of phytotoxicity
2: Small degree of phytotoxicity
3: Moderate degree of phytotoxicity
4: Large degree of phytotoxicity
5: Completely withered

TABLE 1

| Test in a pot in a greenhouse | | | | | | |
|---|---|---|---|---|---|---|
| Active ingredients | | Herbicidal effects observed one month after the treatment with the herbicide | | | | |
| (g/10a) Compound 1 | (g/10a) Compound 2 | DI | SE | AB | AM | ZE |
| 6 | — | 0 | 2 | 0 | 0.5 | 0 |
| 12.5 | — | 0 | 2.5 | 1 | 1 | 0 |
| 25 | — | 0.5 | 4 | 2 | 2 | 0 |
| 50 | — | 1 | 4.5 | 2.5 | 2.5 | 0 |
| — | 12.5 | 0.5 | 0.5 | 1 | 2 | 0 |
| 6 | 12.5 | 2.5 | 4 | 2.5 | 3 | 0 |
| 12.5 | 12.5 | 4 | 4.5 | 3.5 | 3 | 0 |
| 25 | 12.5 | 4.5 | 4.5 | 3.5 | 4 | 0 |
| 50 | 12.5 | 5 | 5 | 5 | 5 | 0 |
| — | 25 | 1.5 | 1 | 2.5 | 3.5 | 0 |
| 6 | 25 | 3 | 4.5 | 4 | 4 | 0 |
| 12.5 | 25 | 4.5 | 5 | 5 | 4.5 | 0 |
| 25 | 25 | 5 | 5 | 5 | 5 | 0 |
| 50 | 25 | 5 | 5 | 5 | 5 | 0 |
| — | 50 | 3 | 2 | 3 | 4 | 0 |
| 6 | 50 | 4 | 5 | 5 | 4.5 | 0 |
| 12.5 | 50 | 5 | 5 | 5 | 5 | 0 |
| 25 | 50 | 5 | 5 | 5 | 5 | 0 |
| 50 | 50 | 5 | 5 | 5 | 5 | 0 |

DI: crabgrass (*Digitaria adscendens*)
SE: greenfoxtail (*Setaria viridis*)
AB: velvetleaf (*Abtilon theophrasti*)
AM: pigweed (*Amaranthus retroflexus*)
ZE: corn (*Zea mays*)

TABLE 2

| Active ingredients | | Herbicidal effects observed one month after the treatment with the herbicide | | | | |
|---|---|---|---|---|---|---|
| (g/10a) Compound 1 | (g/10a) Compound 3 | DI | SE | AB | AM | ZE |
| 6 | — | 0 | 2 | 0 | 0.5 | 0 |
| 12.5 | — | 0 | 2.5 | 1 | 1 | 0 |
| 25 | — | 0.5 | 4 | 2 | 2 | 0 |
| 50 | — | 1 | 4.5 | 2.5 | 2.5 | 0 |
| — | 12.5 | 1.5 | 1 | 2.5 | 1 | 0 |
| 6 | 12.5 | 2.5 | 3.5 | 4 | 3 | 0 |
| 12.5 | 12.5 | 3 | 4.5 | 4.5 | 4.5 | 0 |
| 25 | 12.5 | 3.5 | 5 | 5 | 5 | 0 |
| 50 | 12.5 | 5 | 5 | 5 | 5 | 0 |
| — | 25 | 2.5 | 2 | 4 | 1.5 | 0 |
| 6 | 25 | 3.5 | 4.5 | 4.5 | 4.5 | 0 |
| 12.5 | 25 | 4.5 | 5 | 5 | 5 | 0 |
| 25 | 25 | 5 | 5 | 5 | 5 | 0 |
| 50 | 25 | 5 | 5 | 5 | 5 | 0 |
| — | 50 | 3 | 3 | 4 | 2 | 1 |
| 6 | 50 | 4.5 | 5 | 5 | 5 | 1 |
| 12.5 | 50 | 5 | 5 | 5 | 5 | 1 |
| 25 | 50 | 5 | 5 | 5 | 5 | 1 |
| 50 | 50 | 5 | 5 | 5 | 5 | 1 |

DI: crabgrass (*Digitaria adscendens*)
SE: greenfoxtail (*Setaria viridis*)
AB: velvetleaf (*Abtilon theophrasti*)
AM: pigweed (*Amaranthus retroflexus*)
ZE: corn (*Zea mays*)

TEST EXAMPLE 2

Field Test (Corn)

To a solution having a predetermined concentration of a unitary formulation prepared in accordance with a Formulation Example, a spreader was added so that its concentration would be 300 ppm at the time of application. Such a solution was applied by a manually operated pressure sprayer uniformly at a rate of 50 l/10a over a unit section of 4 m² when various plants had grown therein to 3 to 4 leaf stage in the middle of May.

One month after the application, an investigation was carried out by visual observation. The investigation was carried out by the same evaluation standards as used in Test Example 1. The results are shown in Tables 3 and 4.

TABLE 3

| | | | | Field test (corn) | | | | | | | | | |
|---|---|---|---|---|---|---|---|---|---|---|---|---|---|
| | | | | Dose (g/10a) | | | | Crop | Herbicidal | | | | |
| Formu- | | Content | Amount of | Amounts of active ingredients | | | plant | effects against weeds | | | | | |
| lation | Compounds | (%) | formulation | Comp. 1 | Comp. 2 | Comp. 3 | Corn | DI | SE | AB | AM | XA | IP |
| Composition of the invention | Wettable powder | Compound 1 | 12.5 | 200 | 25 | 50 | — | 0 | 4.5 | 4.5 | 4 | 5 | 5 | 5 |
| | | Compound 2 | 25 | 400 | 50 | 100 | — | 0 | 5 | 5 | 5 | 5 | 5 | 5 |
| | | Compound 1 | 25 | 200 | 50 | 50 | — | 0 | 4.5 | 4.5 | 5 | 5 | 5 | 5 |
| | | Compound 2 | 25 | 400 | 100 | 100 | — | 0 | 5 | 5 | 5 | 5 | 5 | 5 |
| | | Compound 1 | 12.5 | 200 | 25 | 75 | — | 0 | 5 | 5 | 4.5 | 5 | 5 | 5 |
| | | Compound 2 | 37.5 | | | | | | | | | | | |
| | | Compound 1 | 25 | 200 | 50 | 75 | — | 0 | 5 | 5 | 5 | 5 | 5 | 5 |
| | | Compound 2 | 37.5 | | | | | | | | | | | |
| | | Compound 1 | 25 | 400 | 100 | 75 | — | 0 | 5 | 5 | 5 | 5 | 5 | 5 |
| | | Compound 2 | 18.75 | | | | | | | | | | | |
| Comparative (mixture) | Wettable powder | Compound 2 | 25 | 400 | | 100 | | | | | | | | |
| | | Compound A | 18.75 | | Comp. A | 75 | | 1.5 | 4.5 | 4.5 | 4 | 5 | 5 | 5 |

DI: crabgrass (*Digitaria adscendens*)
SB: greenfoxtail (*Setaria viridis*)
AB: velvetleaf (*Abtilon theophrasti*)
AM: pigweed (*Amaranthus retroflexus*)
XA: cocklebur (*Xanthium strumarium*)
IP: morningglory (*Ipomoea* spp)

TABLE 4

| | Formulation | Compounds | Content (%) | Amount of formulation | Dose (g/10a) Amounts of active ingredients | | | Crop plant Corn | Herbicidal effects against weeds | | | | | |
|---|---|---|---|---|---|---|---|---|---|---|---|---|---|---|
| | | | | | Comp. 1 | Comp. 2 | Comp. 3 | | DI | SE | AB | AM | XA | IP |
| Composition of the invention | Granule wettable powder | Compound 1 | 12.5 | 200 | 25 | — | 50 | 0 | 4.5 | 4.5 | 5 | 4 | 5 | 5 |
| | | Compound 3 | 25 | 400 | 50 | — | 100 | 1 | 5 | 5 | 5 | 5 | 5 | 5 |
| | | Compound 1 | 25 | 200 | 50 | — | 50 | 0 | 5 | 5 | 5 | 4.5 | 5 | 5 |
| | | Compound 3 | 25 | 400 | 100 | — | 100 | 1 | 5 | 5 | 5 | 5 | 5 | 5 |
| | | Compound 1 | 12.5 | 200 | 25 | — | 75 | 0 | 5 | 5 | 5 | 4.5 | 5 | 5 |
| | | Compound 3 | 37.5 | | | | | | | | | | | |
| | | Compound 1 | 25 | 200 | 50 | — | 75 | 0 | 5 | 5 | 5 | 5 | 5 | 5 |
| | | Compound 3 | 37.5 | | | | | | | | | | | |
| | | Compound 1 | 25 | 400 | 100 | — | 75 | 1 | 5 | 5 | 5 | 5 | 5 | 5 |
| | | Compound 3 | 18.75 | | | | | | | | | | | |
| Comparative (mixture) | Wettable powder | Compound 3 | 25 | 400 | — | — | 100 | 1.5 | 4.5 | 4.5 | 5 | 3 | 5 | 5 |
| | | Compound A | 18.75 | | Comp. A | 75 | — | | | | | | | |

DI: crabgrass (*Digitaria adscendens*)
SB: greenfoxtail (*Setaria viridis*)
AB: velvetleaf (*Abtilon theophrasti*)
AM: pigweed (*Amaranthus retroflexus*)
XA: cocklebur (*Xanthium strumarium*)
IP: morningglory (Ipomoea spp)

TEST EXAMPLE 3

Field Test (Barley and Wheat)

To a solution having a predetermined concentration of a unitary formulation prepared in accordance with a Formulation Example, a spreader was added so that its concentration would be 300 ppm at the time of application. Such a solution was applied by a manually operated pressure sprayer uniformly at a rate of 50 l/10a over a unit section of 4 m² when various plants had grown therein to 5 to 6 leaf stage in late March.

One month after the application, an investigation was carried out by visual observation. The investigation was carried out by the same evaluation standards as used in Test Example 1. The results are shown in Table 5.

TEST EXAMPLE 4

Field Test (Lawn)

To a solution having a predetermined concentration of a unitary formulation prepared in accordance with a Formulation Example, a spreader was added so that its concentration would be 300 ppm at the time of application. Such a solution was applied by a manually operated pressure sprayer at a rate of 50 l/10a over a unit section of 2 m² when various weeds had grown therein to 3 to 4 leaf stage during the growing stage of lawn in early May.

One month after the application, an investigation was carried out by visual observation. The investigation was conducted by the same evaluation standards as used in

TABLE 5

| | Formulation | Compounds | Content (%) | Amount of formulation | Dose (g/10a) Amounts of active ingredients | | | Crop plant | | Herbicidal effects against weeds | | |
|---|---|---|---|---|---|---|---|---|---|---|---|---|
| | | | | | Comp. 1 | Comp. 2 | Comp. 3 | TR | HO | AL | GA | ST |
| Composition of the invention | Sol | Compound 1 | 25 | 200 | 50 | — | 25 | 0 | 0 | 4.5 | 4.5 | 5 |
| | | Compound 3 | 12.5 | 400 | 100 | — | 50 | 0 | 0 | 5 | 5 | 5 |
| | | Compound 1 | 25 | 200 | 50 | — | 50 | 0 | 0 | 5 | 4.5 | 5 |
| | | Compound 3 | 25 | | | | | | | | | |
| | | Compound 1 | 25 | 400 | 100 | — | 25 | 0 | 0 | 5 | 5 | 5 |
| | | Compound 3 | 6.25 | | | | | | | | | |
| Comparative | Wettable powder | Compound B | 50 | 200 | Compound B | | 100 | 1 | 2 | 4.5 | 4.5 | 5 |

TR: wheat (*Triticum aestivum*)
HO: barley (*Hordeum vulgare*)
AL: water foxtail (*Alopecurus aequalis*)
GA: bedstraw (*Galium aparine*)
ST: chickweed (*Stellaria media*)

Test Example 1. The results are shown in Tables 6 and 7.

TABLE 6

| | Formulation | Compounds | Content (%) | Amount of formulation | Dose (g/10a) Amounts of active ingredients | | | Lawn ZO | Herbicidal effects against weeds | | | |
|---|---|---|---|---|---|---|---|---|---|---|---|---|
| | | | | | Comp. 1 | Comp. 2 | Comp. 3 | | DI | SE | KU | AM |
| Composition of the invention | Granule wettable powder | Compound 1 | 12.5 | 200 | 25 | 50 | — | 0 | 4.5 | 4.5 | 4.5 | 5 |
| | | Compound 2 | 25 | 400 | 50 | 100 | — | 0 | 5 | 5 | 5 | 5 |
| | | Compound 1 | 25 | 200 | 50 | 50 | — | 0 | 4.5 | 4.5 | 4.5 | 5 |
| | | Compound 2 | 25 | 400 | 100 | 100 | — | 0 | 5 | 5 | 5 | 5 |
| | | Compound 1 | 12.5 | 200 | 25 | 75 | — | 0 | 5 | 5 | 5 | 5 |
| | | Compound 2 | 37.5 | 400 | 50 | 150 | — | 0 | 5 | 5 | 5 | 5 |
| | | Compound 1 | 25 | 200 | 50 | 75 | — | 0 | 5 | 5 | 5 | 5 |

TABLE 6-continued

| | Formulation | Compounds | Content (%) | Field test (lawn) | | | | | Herbicidal effects against weeds | | | |
|---|---|---|---|---|---|---|---|---|---|---|---|---|
| | | | | Amount of formulation | Dose (g/10a) Amounts of active ingredients | | | Lawn ZO | DI | SE | KU | AM |
| | | | | | Comp. 1 | Comp. 2 | Comp. 3 | | | | | |
| | | Compound 2 | 37.5 | 400 | 100 | 150 | | 0 | 5 | 5 | 5 | 5 |
| | | Compound 1 | 25 | 400 | 100 | 75 | — | 0 | 5 | 5 | 5 | 5 |
| | | Compound 2 | 18.75 | | | | | | | | | |
| Comparative (single formulation) | Wettable powder | Compound 2 | 50 | 400 | — | 200 | — | 0 | 3.5 | 2 | 3 | 5 |

ZO: *Zoysia Japonica Stend*
DI: crabgrass (*Digitaria adscendens*)
SE: greenfoxtail (*Setaria viridis*)
KU: *Kummerovia striata*
AM: pigweed (*Amaranthus retroflexus*)

TABLE 7

| | Formulation | Compounds | Content (%) | Field test (lawn) | | | | | Herbicidal effects against weeds | | | |
|---|---|---|---|---|---|---|---|---|---|---|---|---|
| | | | | Amount of formulation | Dose (g/10a) Amounts of active ingredients | | | Lawn ZO | DI | SE | KU | AM |
| | | | | | Comp. 1 | Comp. 2 | Comp. 3 | | | | | |
| Composition of the invention | Wettable powder | Compound 1 | 12.5 | 200 | 25 | — | 50 | 0 | 4.5 | 4.5 | 4.5 | 4 |
| | | Compound 3 | 25 | 400 | 50 | — | 100 | 0 | 5 | 5 | 5 | 5 |
| | | Compound 1 | 25 | 200 | 50 | — | 50 | 0 | 5 | 5 | 4.5 | 4.5 |
| | | Compound 3 | 25 | 400 | 100 | — | 100 | 0 | 5 | 5 | 5 | 5 |
| | | Compound 1 | 12.5 | 200 | 25 | — | 75 | 0 | 5 | 5 | 5 | 4.5 |
| | | Compound 3 | 37.5 | 400 | 50 | | 150 | 1 | 5 | 5 | 5 | 5 |
| | | Compound 1 | 25 | 200 | 50 | — | 75 | 0 | 5 | 5 | 5 | 5 |
| | | Compound 3 | 37.5 | 400 | 100 | | 150 | 1 | 5 | 5 | 5 | 5 |
| | | Compound 1 | 25 | 400 | 100 | | 75 | 1 | 5 | 5 | 5 | 5 |
| | | Compound 3 | 18.75 | | | | | | | | | |
| Comparative (single formulation) | Wettable powder | Compound 3 | 50 | 400 | — | — | 200 | 1 | 3 | 2.5 | 5 | 2.5 |

ZO: *Zoysia Japonica Stend*
DI: crabgrass (*Digitaria adscendens*)
SE: greenfoxtail (*Setaria viridis*)
KU: *Kummerovia striata*
AM: pigweed (*Amaranthus retroflexus*)

As is apparent from each of the Test Examples, with the herbicidal composition of the present invention, synergistic effects are obtained by incorporating compound 1 as compared with the dose of a single formulation of compound 2 or 3. Accordingly, it has been made possible to reduce the dose of compound 2 or 3.

Further, by the combination of compound 1 with compound 2 or 3, it has been made possible to completely control broadleaf weeds and gramineous weeds without reducing the selectivity of compound 2 or 3 for crop plants.

TEST EXAMPLE 5

Test in a Pot in a Greenhouse

A solution having a predetermined concentration of a single formulation of compound 1 or a mixture of a single formulation of compound 1 with a single formulation of compound 4 or 5 prepared in accordance with Formulation Example 1, was applied by a spray gun at a rate of 100 l/10a over various plants grown to 3 to 4 leaf stage in a polypropylene pot having a surface area of 150 cm$^2$.

One month after the application, an investigation was carried out by visual observation. The investigation was conducted by the same evaluation standards as used in Test Example 1. The results are shown in Tables 8 and 9.

TABLE 8

| Test in a pot in a greenhouse | | | | | | |
|---|---|---|---|---|---|---|
| Active ingredients | | Herbicidal effects observed one month after the treatment with the herbicide | | | | |
| (g/10a) Compound 1 | (g/10a) Compound 4 | DI | SE | AB | AM | ZE |
| 6 | — | 0 | 2 | 0 | 0.5 | 0 |
| 12.5 | — | 0 | 2.5 | 1 | 1 | 0 |
| 25 | — | 0.5 | 4 | 2 | 2 | 0 |
| 50 | — | 1 | 4.5 | 2.5 | 2.5 | 0 |
| — | 6.3 | 0 | 0 | 1 | 2 | 0 |
| 6 | 6.3 | 0.5 | 3 | 2.5 | 3 | 0 |
| 12.5 | 6.3 | 3 | 4 | 3.5 | 3 | 0 |
| 25 | 6.3 | 4 | 4.5 | 4.5 | 4.5 | 0 |
| 50 | 6.3 | 5 | 5 | 5 | 5 | 0 |
| — | 12.5 | 0 | 0 | 3.5 | 3 | 0 |
| 6 | 12.5 | 2 | 4 | 4.5 | 4.5 | 0 |
| 12.5 | 12.5 | 3 | 4.5 | 5 | 4.5 | 0 |
| 25 | 12.5 | 4.5 | 5 | 5 | 5 | 0 |
| 50 | 12.5 | 5 | 5 | 5 | 5 | 0 |
| — | 25 | 1 | 0 | 4.5 | 4.5 | 1 |
| 6 | 25 | 4 | 4.5 | 5 | 5 | 1 |
| 12.5 | 25 | 4.5 | 5 | 5 | 5 | 1 |
| 25 | 25 | 5 | 5 | 5 | 5 | 1 |
| 50 | 25 | 5 | 5 | 5 | 5 | 1 |

DI: crabgrass (*Digitaria adscendens*)
SE: greenfoxtail (*Setaria viridis*)
AB: velvetleaf (*Abtilon theophrasti*)
AM: pigweed (*Amaranthus retroflexus*)
ZE: corn (*Zea mays*)

TABLE 9

Test in a pot in a greenhouse

| Active ingredients (g/10a) | | Herbicidal effects observed one month after the treatment with the herbicide | | | | |
|---|---|---|---|---|---|---|
| Compound 1 | Compound 5 | DI | SE | AB | AM | ZE |
| 6 | — | 0 | 2 | 0 | 0.5 | 0 |
| 12.5 | — | 0 | 2.5 | 1 | 1 | 0 |
| 25 | — | 0.5 | 4 | 2 | 2 | 0 |
| 50 | — | 1 | 4.5 | 2.5 | 2.5 | 0 |
| — | 6.3 | 0.5 | 0 | 2 | 3 | 0 |
| 6 | 6.3 | 2.5 | 3.5 | 4 | 4 | 0 |
| 12.5 | 6.3 | 3 | 4.5 | 4.5 | 4.5 | 0 |
| 25 | 6.3 | 4 | 5 | 5 | 5 | 0 |
| 50 | 6.3 | 5 | 5 | 5 | 5 | 0 |
| — | 12.5 | 2 | 0 | 3.5 | 4 | 0.5 |
| 6 | 12.5 | 3 | 4.5 | 4.5 | 4.5 | 0.5 |
| 12.5 | 12.5 | 3.5 | 5 | 5 | 5 | 0.5 |
| 25 | 12.5 | 4.5 | 5 | 5 | 5 | 0.5 |
| 50 | 12.5 | 5 | 5 | 5 | 5 | 0.5 |
| — | 25 | 2.5 | 0.5 | 4.5 | 4.5 | 1 |
| 6 | 25 | 3 | 4.5 | 5 | 5 | 1 |
| 12.5 | 25 | 3.5 | 5 | 5 | 5 | 1 |
| 25 | 25 | 4.5 | 5 | 5 | 5 | 1 |
| 50 | 25 | 5 | 5 | 5 | 5 | 1 |

DI: crabgrass (Digitaria adscendens)
SE: greenfoxtail (Setaria viridis)
AB: velvetleaf (Abtilon theophrasti)
AM: pigweed (Amaranthus retroflexus)
ZE: corn (Zea mays)

TEST EXAMPLE 6

Field Test (Corn)

A solution having a predetermined concentration of a unitary formulation prepared in accordance with a Formulation Example, was applied by a manually operated pressure sprayer uniformly at a rate of 50 l/10a over a unit section of 4 m² when various plants had grown therein to 3 to 4 leaf stage in the middle of May.

One month after the application, an investigation was carried out by visual observation. The investigation was conducted by the same evaluation standards as used in Test Example 1. The results are shown in Tables 10 and 11.

TABLE 10

Field test (corn)

| | Formulation | Compounds | Content (%) | Amount of formulation | Dose (g/10a) Amounts of active ingredients | | | Crop plant | Herbicidal effects against weeds | | | | | |
|---|---|---|---|---|---|---|---|---|---|---|---|---|---|---|
| | | | | | Comp. 1 | Comp. 4 | Comp. 5 | Corn | DI | SE | AB | AM | XA | IP |
| Composition of the invention | Wettable powder | Compound 1 | 25 | 200 | 50 | 20 | — | 0 | 4 | 4.5 | 5 | 5 | 5 | 5 |
| | | Compound 4 | 10 | | | | | | | | | | | |
| | | Compound 1 | 25 | 200 | 50 | 25 | — | 0 | 4 | 4.5 | 5 | 5 | 5 | 5 |
| | | Compound 4 | 12.5 | | | | | | | | | | | |
| | | Compound 1 | 37.5 | 200 | 75 | 20 | — | 0 | 4 | 4.5 | 5 | 5 | 5 | 5 |
| | | Compound 4 | 10 | | | | | | | | | | | |
| | | Compound 1 | 37.5 | 200 | 75 | 25 | — | 0 | 4.5 | 5 | 5 | 5 | 5 | 5 |
| | | Compound 4 | 12.5 | | | | | | | | | | | |
| | | Compound 1 | 50 | 400 | 100 | 20 | — | 0 | 4.5 | 5 | 5 | 5 | 5 | 5 |
| | | Compound 4 | 10 | | | | | | | | | | | |
| | | Compound 1 | 50 | 200 | 100 | 25 | — | 0 | 5 | 5 | 5 | 5 | 5 | 5 |
| | | Compound 4 | 12.5 | | | | | | | | | | | |
| Comparative | Emulsion | Compound 4 | 25 | 100 | | 25 | | 0 | 0 | 0 | 5 | 5 | 5 | 4.5 |
| Comparative | Wettable powder | Compound 2 | 50 | 200 | | | | 0 | 3 | 4 | 3.5 | 5 | 4.5 | 4.5 |

DI: crabgrass (Digitaria adscendens)
SE: greenfoxtail (Setaria viridis)
AB: velvetleaf (Abtilon theophrasti)
AM: pigweed (Amaranthus retroflexus)
XA: cocklebur (Xanthium strumarium)
IP: morningglory (Ipomoea spp)

TABLE 11

Field test (corn)

| | Formulation | Compounds | Content (%) | Amount of formulation | Dose (g/10a) Amounts of active ingredients | | | Crop plant | Herbicidal effects against weeds | | | | | |
|---|---|---|---|---|---|---|---|---|---|---|---|---|---|---|
| | | | | | Comp. 1 | Comp. 4 | Comp. 5 | Corn | DI | SE | AB | AM | XA | IP |
| Composition of the invention | Granule wettable powder | Compound 1 | 25 | 200 | 50 | — | 20 | 0 | 4 | 4 | 5 | 5 | 5 | 5 |
| | | Compound 5 | 10 | | | | | | | | | | | |
| | | Compound 1 | 25 | 200 | 50 | — | 25 | 0.5 | 4 | 4.5 | 5 | 5 | 5 | 5 |
| | | Compound 5 | 12.5 | | | | | | | | | | | |
| | | Compound 1 | 37.5 | 200 | 75 | — | 20 | 0 | 4.5 | 4 | 5 | 5 | 5 | 5 |
| | | Compound 5 | 10 | | | | | | | | | | | |
| | | Compound 1 | 37.5 | 200 | 75 | — | 25 | 0.5 | 4.5 | 5 | 5 | 5 | 5 | 5 |
| | | Compound 5 | 12.5 | | | | | | | | | | | |
| | | Compound 1 | 50 | 200 | 100 | — | 20 | 0 | 4.5 | 4.5 | 5 | 5 | 5 | 5 |
| | | Compound 5 | 10 | | | | | | | | | | | |
| | | Compound 1 | 50 | 200 | 100 | — | 25 | 0.5 | 5 | 5 | 5 | 5 | 5 | 5 |
| | | Compound 5 | 12.5 | | | | | | | | | | | |

TABLE 11-continued

| | | | | Field test (corn) | | | | | | | | | |
|---|---|---|---|---|---|---|---|---|---|---|---|---|---|
| | | | | Dose (g/10a) | | | Crop plant | Herbicidal effects against weeds | | | | | |
| | Formulation | Compounds | Content (%) | Amount of formulation | Amounts of active ingredients | | | | | | | | |
| | | | | | Comp. 1 | Comp. 4 | Comp. 5 | Corn | DI | SE | AB | AM | XA | IP |
| Comparative | Emulsion | Compound 5 | 25 | 100 | | | 25 | 0.5 | 0.5 | 0 | 5 | 5 | 4.5 | 5 |

DI: crabgrass (*Digitaria adscendens*)
SE: greenfoxtail (*Setaria viridis*)
AB: velvetleaf (*Abtilon theophrasti*)
AM: pigweed (*Amaranthus retroflexus*)
XA: cocklebur (*Xanthium strumarium*)
IP: morningglory (Ipomoea spp)

TEST EXAMPLE 7
Field Test (Barley and Wheat)

A solution having a predetermined concentration of a unitary formulation prepared in accordance with a Formulation Example, was applied by a manually operated pressure sprayer uniformly at a rate of 50 l/10a over a unit section of 4 m² when various plants had grown therein to 5 to 6 leaf stage in late March.

One month after the application, an investigation was carried out by visual observation. The investigation was conducted by the same evaluation standards as used in Test Example 1. The results are shown in Table 12.

TEST EXAMPLE 8
Field Test (*Zoysia metrella*)

A solution having a predetermined concentration of a unitary formulation prepared in accordance with a Formulation Example, was applied by a manually operated pressure sprayer uniformly at a rate of 50 l/10a over a unit section of 2 m² when various weeds had grown therein to 3 to 4 leaf stage during the growing stage of lawn in early May.

One month after the application, an investigation was carried out by visual observation. The investigation was conducted by the same evaluation standards as used in Test Example 1. The results are shown in Tables 13 and 14.

TABLE 12

| | | | | Field test (barley and wheat) | | | | | | | | |
|---|---|---|---|---|---|---|---|---|---|---|---|---|
| | | | | Dose (g/10a) | | | | Crop plant | | Herbicidal effects against weeds | | |
| | Formulation | Compounds | Content (%) | Amount of formulation | Amounts of active ingredients | | | | | | | |
| | | | | | Comp. 1 | Comp. 4 | Comp. 5 | TR | HO | AI | GA | ST |
| Composition of the invention | Emulsion | Compound 1 | 25 | 400 | 100 | 25 | — | 0 | 1 | 4 | 4 | 5 |
| | | Compound 4 | 6.25 | | | | | | | | | |
| | | Compound 1 | 37.5 | 400 | 150 | 25 | — | 0 | 1 | 4.5 | 4.5 | 5 |
| | | Compound 4 | 6.25 | | | | | | | | | |
| | | Compound 1 | 50 | 400 | 200 | 25 | — | 0 | 1 | 5 | 5 | 5 |
| | | Compound 4 | 6.25 | | | | | | | | | |
| Comparative | Wettable powder | Compound 4 | 25 | 100 | | 25 | | 0 | 1 | 0 | 3 | 5 |
| Comparative | Wettable powder | Compound B | 50 | 200 | Compound B | | 100 | 1 | 2 | 4.5 | 4 | 5 |

TR: wheat (*Triticum aestivum*)
HO: barley (*Hordeum vulgare*)
AL: water foxtail (*Alopecurus aequalis*)
GA: bedstraw (*Galium aparine*)
ST: chickweed (*Stellaria media*)

TABLE 13

| | | | | Field test (lawn) | | | | | | | | |
|---|---|---|---|---|---|---|---|---|---|---|---|---|
| | | | | Dose (g/10a) | | | | Lawn | Herbicidal effects against weeds | | | |
| | Formulation | Compounds | Content (%) | Amount of formulation | Amounts of active ingredients | | | | | | | |
| | | | | | Comp. 1 | Comp. 4 | Comp. 5 | ZO | DI | SE | KU | AM |
| Composition of the invention | Granule wettable powder | Compound 1 | 25 | 200 | 50 | 20 | — | 0 | 3 | 3.5 | 4 | 4.5 |
| | | Compound 4 | 10 | | | | | | | | | |
| | | Compound 1 | 25 | 200 | 50 | 25 | — | 0 | 3 | 4 | 4.5 | 5 |
| | | Compound 4 | 12.5 | | | | | | | | | |
| | | Compound 1 | 37.5 | 200 | 75 | 20 | — | 0 | 4 | 4 | 5 | 5 |
| | | Compound 4 | 10 | | | | | | | | | |
| | | Compound 1 | 37.5 | 200 | 75 | 25 | — | 0 | 4.5 | 4.5 | 5 | 5 |
| | | Compound 4 | 12.5 | | | | | | | | | |
| | | Compound 1 | 50 | 200 | 100 | 20 | — | 0 | 4.5 | 4.5 | 5 | 5 |
| | | Compound 4 | 10 | | | | | | | | | |
| | | Compound 1 | 50 | 200 | 100 | 25 | — | 0 | 5 | 5 | 5 | 5 |
| | | Compound 4 | 12.5 | | | | | | | | | |
| Comparative (single | Wettable powder | Compound 4 | 25 | 100 | — | 25 | — | 0 | 0 | 0 | 3 | 3 |

TABLE 13-continued

|  |  |  | Field test (lawn) | | | | | | | | |
|---|---|---|---|---|---|---|---|---|---|---|---|
|  |  |  |  | Dose (g/10a) | | | | Herbicidal effects | | | |
|  |  | Content | Amount of | Amounts of active ingredients | | | Lawn | against weeds | | | |
| Formulation | Compounds | (%) | formulation | Comp. 1 | Comp. 4 | Comp. 5 | ZO | DI | SE | KU | AM |
| formulation) |  |  |  |  |  |  |  |  |  |  |  |

ZO: *Zoysia Japonica Stend*
DI: crabgrass (*Digitaria adscendens*)
SE: greenfoxtail (*Setaria viridis*)
KU: *Kummerovia striata*
AM: pigweed (*Amaranthus retroflexus*)

TABLE 14

|  |  |  |  | Field test (lawn) | | | | | | | |
|---|---|---|---|---|---|---|---|---|---|---|---|
|  |  |  |  | Dose (g/10a) | | | | Herbicidal effects | | | |
|  |  |  | Content | Amount of | Amounts of active ingredients | | Lawn | against weeds | | | |
|  | Formulation | Compounds | (%) | formulation | Comp. 1 | Comp. 4 | Comp. 5 | ZO | DI | SE | KU | AM |
| Composition of the invention | Wettable powder | Compound 1 | 25 | 200 | 50 | — | 20 | 0 | 3.5 | 4 | 4 | 4 |
|  |  | Compound 5 | 10 |  |  |  |  |  |  |  |  |  |
|  |  | Compound 1 | 25 | 200 | 50 | — | 25 | 0 | 4 | 4.5 | 5 | 5 |
|  |  | Compound 5 | 12.5 |  |  |  |  |  |  |  |  |  |
|  |  | Compound 1 | 37.5 | 200 | 75 | — | 20 | 0 | 4 | 4.5 | 4 | 4.5 |
|  |  | Compound 5 | 10 |  |  |  |  |  |  |  |  |  |
|  |  | Compound 1 | 37.5 | 200 | 75 | — | 25 | 0 | 4.5 | 5 | 5 | 5 |
|  |  | Compound 5 | 12.5 |  |  |  |  |  |  |  |  |  |
|  |  | Compound 1 | 50 | 200 | 100 | — | 20 | 0 | 4.5 | 5 | 5 | 5 |
|  |  | Compound 5 | 10 |  |  |  |  |  |  |  |  |  |
|  |  | Compound 1 | 50 | 200 | 100 | — | 25 | 0 | 5 | 5 | 5 | 5 |
|  |  | Compound 5 | 12.5 |  |  |  |  |  |  |  |  |  |
| Comparative (single formulation) | Wettable powder | Compound 5 | 25 | 100 | — | — | 25 | 0 | 1 | 0.5 | 3 | 3.5 |

ZO: *Zoysia Japonica Stend*
DI: crabgrass (*Digitaria adscendens*)
SE: greenfoxtail (*Setaria viridis*)
KU: *Kummerovia striata*
AM: pigweed (*Amaranthus retroflexus*)

With the herbicidal composition of the present invention wherein compound 1 is combined with compound 4 or 5, it is possible to completely control broadleaf weeds and gramineous weeds without reducing the selectivity of compound 4 or 5 for crop plants.

TEST EXAMPLE 9

Test in a Pot in a Greenhouse

A solution having a predetermined concentration of a single formulation of compound 1 or a mixture of a single formulation of compound 1 with a single formulation of compound 6 prepared in accordance with Formulation Example 1, was applied by a spray gun at a rate of 100 l/10a over various plants grown to 3 to 4 leaf stage in a polypropylene pot having a surface area of 150 cm$^2$.

One month after the application, an investigation was carried out by visual observation. The investigation was conducted by the same evaluation standards as used in Test Example 1. The results are shown in Table 15.

TABLE 15

| Test in a pot in a greenhouse | | | | | | |
|---|---|---|---|---|---|---|
| Active ingredients | | Herbicidal effects observed one month after the treatment with the herbicide | | | | |
| (g/10a) | (g/10a) | | | | | |
| Compound 1 | Compound 6 | DI | SE | AB | AM | ZE |
| 6 | — | 0 | 2 | 0 | 0 | 0 |
| 12.5 | — | 0 | 2.5 | 1 | 0 | 0 |
| 25 | — | 0.5 | 4 | 2 | 1 | 0 |
| 50 | — | 1 | 4.5 | 2.5 | 2 | 0 |
| — | 12.5 | 3 | 0 | 1.5 | 0 | 0 |
| 6 | 12.5 | 4 | 3 | 2.5 | 1 | 0 |
| 12.5 | 12.5 | 4 | 3 | 2.5 | 2.5 | 0 |

TABLE 15-continued

| Test in a pot in a greenhouse | | | | | | |
|---|---|---|---|---|---|---|
| Active ingredients | | Herbicidal effects observed one month after the treatment with the herbicide | | | | |
| (g/10a) | (g/10a) | | | | | |
| Compound 1 | Compound 6 | DI | SE | AB | AM | ZE |
| 25 | 12.5 | 4.5 | 5 | 3.5 | 4 | 0 |
| 50 | 12.5 | 5 | 5 | 4 | 4.5 | 0 |
| — | 25 | 3.5 | 0 | 2 | 1 | 0 |
| 6 | 25 | 4 | 3.5 | 2.5 | 2 | 0 |
| 12.5 | 25 | 4.5 | 4 | 3.5 | 2.5 | 0 |
| 25 | 25 | 5 | 5 | 4.5 | 4.5 | 0 |
| 50 | 25 | 5 | 5 | 5 | 5 | 0 |
| — | 50 | 4 | 1 | 2.5 | 2 | 0 |
| 6 | 50 | 4.5 | 4.5 | 3.5 | 3 | 0 |
| 12.5 | 50 | 5 | 5 | 4.5 | 4 | 0 |
| 25 | 50 | 5 | 5 | 5 | 5 | 0 |
| 50 | 50 | 5 | 5 | 5 | 5 | 0 |

DI: crabgrass (*Digitaria adscendens*)
SE: greenfoxtail (*Setaria viridis*)
AB: velvetleaf (*Abtilon theophrasti*)
AM: pigweed (*Amaranthus retroflexus*)
ZE: corn (*Zea mays*)

TEST EXAMPLE 10

Field Test (Corn)

A solution having a predetermined concentration of a unitary formulation prepared in accordance with a Formulation Example, was applied by a manually operated pressure sprayer uniformly at a rate of 50 l/10a over a unit section of 4 m$^2$ when various plants had grown therein to 3 to 4 leaf stage in the middle of May.

One month after the application, an investigation was carried out by visual observation. The investigation was conducted by the same evaluation standards as used in Test Example 1. The results are shown in Table 16.

TABLE 16

| | | | | Field test (corn) Dose (g/10a) | | | | | | | | | |
|---|---|---|---|---|---|---|---|---|---|---|---|---|---|
| | | | | | Amounts of active ingredients | | Crop plant | Herbicidal effects against weeds | | | | | |
| | Formulation | Compounds | Content (%) | Amount of formulation | Comp. 1 | Comp. 6 | Corn | DI | SE | AB | AM | CH | SO |
| Composition of the invention | Emulsion | Compound 1 Compound 6 | 25 15 | 200 | 50 | 20 | 0 | 4 | 4 | 4 | 4.5 | 4.5 | 4 |
| | | Compound 1 Compound 6 | 25 22.5 | 200 | 50 | 45 | 0 | 4 | 4.5 | 4 | 4.5 | 5 | 4 |
| | Sol | Compound 1 Compound 6 | 37.5 15 | 200 | 75 | 30 | 0 | 4.5 | 4 | 4 | 4.5 | 5 | 4 |
| | | Compound 1 Compound 6 | 37.5 22.5 | 200 | 75 | 45 | 0 | 4.5 | 5 | 5 | 5 | 5 | 5 |
| | Granule wettable powder | Compound 1 Compound 6 | 50 15 | 400 | 100 | 30 | 0 | 4.5 | 5 | 5 | 5 | 5 | 5 |
| | | Compound 1 Compound 6 | 50 22.5 | 200 | 100 | 45 | 0 | 5 | 5 | 5 | 5 | 5 | 5 |
| Comparative | Wettable powder | Compound 6 | 45 | 100 | | 45 | 0 | 3.5 | 0 | 3 | 4 | 4.5 | 3.5 |
| Comparative | Wettable powder | Compound 2 | 50 | 200 | | | 0 | 4 | 4 | 3.5 | 5 | 5 | 5 |

DI: crabgrass (*Digitaria adscendens*)
SE: greenfoxtail (*Setaria viridis*)
AB: velvetleaf (*Abtilon theophrasti*)
AM: pigweed (*Amaranthus retroflexus*)
CH: lambsquater (*Chenopodium album*)
SO: black nightshade (*Solanum nigrum* L.)

With the herbicidal composition of the present invention wherein compounds 1 and 6 are combined, it is possible to completely control broadleaf weeds and gramineous weeds without reducing the selectivity of compound 6 for crop plants.

TEST EXAMPLE 11

Test in a Pot in a Greenhouse

A solution having a predetermined concentration of a single formulation of compound 1 or a mixture of a single formulation of compound 1 with a single formulation of compound 7 prepared in accordance with Formulation Example 1, was applied by a spray gun at a rate of 100 l/10a over various plants grown to 3 to 4 leaf stage in a polypropylene pot having a surface area of 150 cm$^2$.

One month after the application, an investigation was carried out by visual observation. The investigation was conducted by the same evaluation standards as used in Test Example 1. The results are shown in Table 17.

TABLE 17

| Test in a pot in a greenhouse | | | | | | |
|---|---|---|---|---|---|---|
| Active ingredients | | Herbicidal effects observed one month after the treatment with the herbicide | | | | |
| (g/10a) Compound 1 | (g/10a) Compound 7 | DI | SE | AB | AM | ZE |
| 6 | — | 0 | 2 | 0 | 0 | 0 |
| 12.5 | — | 0 | 2.5 | 1 | 0 | 0 |
| 25 | — | 0.5 | 4 | 2 | 1 | 0 |
| 50 | — | 1 | 4.5 | 2.5 | 2 | 0 |
| — | 5 | 0 | 0 | 3.5 | 4 | 0 |
| 6 | 5 | 2 | 3 | 4 | 4.5 | 0 |

TABLE 17-continued

| Test in a pot in a greenhouse | | | | | | |
|---|---|---|---|---|---|---|
| Active ingredients | | Herbicidal effects observed one month after the treatment with the herbicide | | | | |
| (g/10a) Compound 1 | (g/10a) Compound 7 | DI | SE | AB | AM | ZE |
| 12.5 | 5 | 3 | 3.5 | 4.5 | 5 | 0 |
| 25 | 5 | 4.5 | 4.5 | 5 | 5 | 0 |
| 50 | 5 | 5 | 5 | 5 | 5 | 0 |
| — | 10 | 0 | 0 | 4 | 4.5 | 0 |
| 6 | 10 | 3 | 4 | 4.5 | 5 | 0 |
| 12.5 | 10 | 4.5 | 4.5 | 5 | 5 | 0 |
| 25 | 10 | 5 | 5 | 5 | 5 | 0 |
| 50 | 10 | 5 | 5 | 5 | 5 | 0 |
| — | 20 | 1 | 1 | 4.5 | 5 | 2 |
| 6 | 20 | 4.5 | 5 | 5 | 5 | 2 |
| 12.5 | 20 | 5 | 5 | 5 | 5 | 2 |
| 25 | 20 | 5 | 5 | 5 | 5 | 2 |
| 50 | 20 | 5 | 5 | 5 | 5 | 2 |

DI: crabgrass (*Digitaria adscendens*)
SE: greenfoxtail (*Setaria viridis*)
AB: velvetleaf (*Abtilon theophrasti*)
AM: pigweed (*Amaranthus retroflexus*)
ZE: corn (*Zea mays*)

TEST EXAMPLE 12

Field Test (Corn)

A solution having a predetermined concentration of a unitary formulation prepared in accordance with a Formulation Example, was applied by a manually operated pressure sprayer uniformly at a rate of 50 l/10a over a unit section of 4 m$^2$ when various plants had grown therein to 3 to 4 leaf stage in the middle of May.

One month after the application, an investigation was carried out by visual observation. The investigation was conducted by the same evaluation standards as used in Test Example 1. The results are shown in Table 18.

TABLE 18

| | | | | Field test (corn) Dose (g/10a) | | | | | | | | | |
|---|---|---|---|---|---|---|---|---|---|---|---|---|---|
| | | | | | Amounts of active ingredients | | Crop plant | Herbicidal effects against weeds | | | | | |
| | Formulation | Compounds | Content (%) | Amount of formulation | Comp. 1 | Comp. 7 | Corn | DI | SE | AB | AM | XA | IP |
| Composition of the | Emulsion | Compound 1 Compound 7 | 25 3.75 | 200 | 50 | 7.5 | 0 | 4 | 4 | 4.5 | 4.5 | 4.5 | 4 |

TABLE 18-continued

| | | | | Field test (corn) | | | | | | | | |
| | | | | Dose (g/10a) | | | | | | | | |
| | Formulation | Compounds | Content (%) | Amount of formulation | Amounts of active ingredients | | Crop plant | Herbicidal effects against weeds | | | | | |
| | | | | | Comp. 1 | Comp. 7 | Corn | DI | SE | AB | AM | XA | IP |
|---|---|---|---|---|---|---|---|---|---|---|---|---|---|
| invention | | Compound 1 | 25 | 200 | 50 | 10 | 0 | 4 | 4.5 | 5 | 5 | 5 | 4 |
| | | Compound 7 | 5 | | | | | | | | | | |
| | Sol | Compound 1 | 37.5 | 200 | 75 | 7.5 | 0 | 4.5 | 4 | 4.5 | 4.5 | 5 | 4.5 |
| | | Compound 7 | 3.75 | | | | | | | | | | |
| | | Compound 1 | 37.5 | 200 | 75 | 10 | 0 | 4.5 | 5 | 5 | 5 | 5 | 5 |
| | | Compound 7 | 5 | | | | | | | | | | |
| | Granule wettable powder | Compound 1 | 50 | 400 | 100 | 7.5 | 0 | 4.5 | 5 | 5 | 5 | 5 | 5 |
| | | Compound 7 | 3.75 | | | | | | | | | | |
| | | Compound 1 | 50 | 200 | 100 | 10 | 0 | 5 | 5 | 5 | 5 | 5 | 5 |
| | | Compound 7 | 5 | | | | | | | | | | |
| Comparative | Wettable powder | Compound 7 | 5 | 100 | | 10 | 0 | 0 | 0 | 3 | 4 | 4.5 | 3.5 |
| Comparative | Wettable powder | Compound 2 | 50 | 200 | | | 0 | 4 | 3.5 | 3.5 | 5 | 4.5 | 5 |

DI: crabgrass (*Digitaria adscendens*)
SE: greenfoxtail (*Setaria viridis*)
AB: velvetleaf (*Abtilon theophrasti*)
AM: pigweed (*Amaranthus retroflexus*)
XA: cocklebur (*Xanthium strumarium*)
IP: morningglory (*Ipomoea hederacea*)

With the herbicidal composition of the present invention wherein compounds 1 and 7 are combined, it is possible to completely control broadleaf weeds and gramineous weeds without reducing the selectivity of compound 7 for crop plants.

We claim:

1. A herbicidal composition for upland fields, which consists essentially of, as active ingredients, a combination of 2',3'-dichloro-4-ethoxymethoxybenzanilide (compound 1) with one member selected from the group consisting of 2-chloro-4-ethylamino-6-isopropylamino-1,3,5-triazine (compound 2), 2-(4-chloro-6-ethylamino-1,3,5-triazin-2-yl)amino-2-methylpropiononitrile (compound 3), 4-hydroxy-3,5-diiodobenzonitrile (compound 4), 4-octanoyloxy-3,5-dibromobenzonitrile (compound 5), and 4-amino-6-tert-butyl-3-methylthio-1,2,4-triazine-5(4H)-one (compound 7).

2. The herbicidal composition according to claim 1, which comprises compounds 1 and 2, wherein the weight ratio of compound 1:compound 2 is from 1:0.1 to 1:10.

3. The herbicidal composition according to claim 1, which comprises compounds 1 and 3, wherein the weight ratio of compound 1:compound 3 is from 1:0.1 to 1:10.

4. The herbicidal composition according to claim 1, which comprises compounds 1 and 4, wherein the weight ratio of compound 1:compound 4 is from 1:0.01 to 1:1.

5. The herbicidal composition according to claim 1, which comprises compounds 1 and 5, wherein the weight ratio of compound 1:compound 5 is from 1:0.01 to 1:1.

6. The herbicidal composition according to claim 1, which comprises compounds 1 and 7, wherein the weight ratio of compound 1:compound 7 is from 1:0.01 to 1:1.

7. The herbicidal composition according to claim 1, wherein from 10 to 200 g/10a of compound 1 is combined with from 10 to 200 g/10a of compound 2 or 3, from 5 to 100 g/10a of compound 4 or 5, or from 1 to 25 g/10a of compound 7.

* * * * *